(12) United States Patent
Voutilainen

(10) Patent No.: US 10,491,407 B2
(45) Date of Patent: Nov. 26, 2019

(54) PHYSICAL UNCLONABLE FUNCTION

(71) Applicant: Nokia Technologies Oy, Espoo (FI)

(72) Inventor: Martti Voutilainen, Espoo (FI)

(73) Assignee: Nokia Technologies Oy, Espoo (FI)

(*) Notice: Subject to any disclaimer, the term of this patent is extended or adjusted under 35 U.S.C. 154(b) by 138 days.

(21) Appl. No.: 15/502,361

(22) PCT Filed: Aug. 13, 2014

(86) PCT No.: PCT/FI2014/050621
§ 371 (c)(1),
(2) Date: Feb. 7, 2017

(87) PCT Pub. No.: WO2016/024037
PCT Pub. Date: Feb. 18, 2016

(65) Prior Publication Data
US 2017/0230188 A1    Aug. 10, 2017

(51) Int. Cl.
*H04L 9/32* (2006.01)
*G09C 1/00* (2006.01)
(Continued)

(52) U.S. Cl.
CPC ............ *H04L 9/3278* (2013.01); *B82Y 10/00* (2013.01); *B82Y 15/00* (2013.01); *G09C 1/00* (2013.01);
(Continued)

(58) Field of Classification Search
CPC ............... H04L 9/3278; H04L 2209/80; H04L 2209/12; H01L 29/1606; H01L 2209/12;
(Continued)

(56) References Cited

U.S. PATENT DOCUMENTS

2003/0136837 A1* 7/2003 Amon ............... G07D 7/04
235/435
2005/0056695 A1  3/2005 Hartmann et al.
(Continued)

FOREIGN PATENT DOCUMENTS

CN    1867924 A    11/2006
CN    104169851 A    11/2014
(Continued)

OTHER PUBLICATIONS

Chakraborty et al., A Transmission Gate Physical Unclonable Function and On-Chip Voltageto-Digital Conversion Technique, 10 pages (Year: 2013).*
(Continued)

*Primary Examiner* — Huan V Doan
(74) *Attorney, Agent, or Firm* — Harrington & Smith

(57) ABSTRACT

Apparatus, electronic device, system and method comprising a first element (102) configured to receive a first signal and convert the first signal to a second signal, a second element (104) configured to relay the second signal to a third element (106, 108), the third element (106, 108) being configured to convert the second signal to a third signal and to send the third signal; wherein the first element (102) is configured to convert the first signal to the second signal in such a way that the conversion is dependent on the physiochemical structure of at least part of the first element (102). In some embodiments the first element comprises a photoacoustic sensor comprising at least one graphene layer, the second element comprises a mechanical wave transmission line, and the third element comprises carbon nanotube antennas.

15 Claims, 3 Drawing Sheets

(51) Int. Cl.
  *H01L 23/00*  (2006.01)
  *B82Y 10/00*  (2011.01)
  *B82Y 15/00*  (2011.01)
  *G01N 21/17*  (2006.01)
  *G01N 21/3581*  (2014.01)
  *H01L 29/16*  (2006.01)

(52) U.S. Cl.
  CPC ........ *H01L 23/573* (2013.01); *G01N 21/1702* (2013.01); *G01N 21/3581* (2013.01); *H01L 29/1606* (2013.01); *H04L 2209/12* (2013.01); *H04L 2209/80* (2013.01)

(58) Field of Classification Search
  CPC ... H01L 2209/80; H01L 23/573; B82Y 15/00; B82Y 10/00; G09C 1/00; G01N 21/3581; G01N 21/1702
  See application file for complete search history.

(56) References Cited

U.S. PATENT DOCUMENTS

| | | | |
|---|---|---|---|
| 2006/0202802 | A1 | 9/2006 | Seppa |
| 2007/0105240 | A1* | 5/2007 | Kempa ................. B82Y 20/00 438/3 |
| 2007/0139165 | A1 | 6/2007 | Liu |
| 2009/0239468 | A1* | 9/2009 | He ...................... H04L 63/0853 455/41.2 |
| 2010/0171596 | A1 | 7/2010 | Burke et al. |
| 2010/0271003 | A1 | 10/2010 | Jensen et al. |
| 2010/0315153 | A1* | 12/2010 | Oksanen ................ B82Y 10/00 327/535 |
| 2011/0099117 | A1* | 4/2011 | Schepers .............. G06F 21/305 705/318 |
| 2012/0065930 | A1* | 3/2012 | Allee ..................... G01B 11/00 702/150 |
| 2012/0145890 | A1* | 6/2012 | Goodlett ............. H01J 49/0454 250/282 |
| 2012/0255860 | A1* | 10/2012 | Briman ................... H01B 1/04 204/403.15 |
| 2012/0298623 | A1 | 11/2012 | Jiang et al. |
| 2013/0050047 | A1* | 2/2013 | Carr ....................... H01Q 1/248 343/853 |
| 2013/0322617 | A1* | 12/2013 | Orshansky ........... H04L 9/3278 380/28 |
| 2014/0033822 | A1 | 2/2014 | Yoon et al. |
| 2014/0108786 | A1 | 4/2014 | Kreft |
| 2014/0112107 | A1 | 4/2014 | Guo et al. |
| 2014/0145426 | A1 | 5/2014 | Lettow et al. |
| 2014/0159040 | A1* | 6/2014 | Dimitrakopoulos ........................ H01L 21/02225 257/48 |
| 2014/0351073 | A1* | 11/2014 | Murphy ................ G06Q 10/00 705/23 |

FOREIGN PATENT DOCUMENTS

| | | |
|---|---|---|
| EP | 2230794 A2 | 9/2010 |
| EP | 2237183 A1 | 10/2010 |
| EP | 2626816 A1 | 8/2013 |
| WO | 2010/076733 A1 | 7/2010 |
| WO | 2013/117815 A1 | 8/2013 |
| WO | 2014/019678 A1 | 2/2014 |

OTHER PUBLICATIONS

"Physical Unclonable Function", Wikipedia, Retrieved on Jan. 10, 2016, Webpage available at : https://en.wikipedia.org/wiki/Physical_unclonable_function.

Mehulkumar et al., "Direct Production of Graphene Nanosheets for Near Infrared Photoacoustic Imaging", American Chemical Society, vol. 7, No. 9, 2013, 2 pages.

Wang et al., "Novel Physical Unclonable Function With Process and Environmental Variations", Proceedings of the Conference on Design, Automation and Test in Europe, Mar. 8-12, 2010, pp. 1065-1070.

International Search Report and Written Opinion received for corresponding Patent Cooperation Treaty Application No. PCT/FI2014/050621, dated Feb. 11, 2015, 22 pages.

Habraken et al., "Continuous Mode Cooling and Phonon Routers for Phononic Quantum Networks", New Journal of Physics, vol. 14, Nov. 2012, pp. 1-32.

"Acoustic Metamaterials", Wikipedia, Retrieved on Jan. 10, 2016, Webpage available at : https://en.wikipedia.org/wiki/Acoustic_metamaterial.

Extended European Search Report received for corresponding European Patent Application No. 14899654.9, dated Mar. 28, 2018, 9 pages.

Voutilainen et al., "Graphene and Carbon Nanotube Applications in Mobile Devices", IEEE Transactions on Electron Devices, vol. 59, No. 11, Nov. 2012, pp. 2876-2887.

Voutilainen et al., "Physics of Proximity Josephson Sensor", Journal of Applied Physics, vol. 107, No. 6 Jun. 30, 2009, pp. 1-13.

* cited by examiner

PHYSICAL UNCLONABLE FUNCTION

RELATED APPLICATION

This application was originally filed as PCT Application No. PCT/FI2014/050621 filed Aug. 13, 2014.

TECHNICAL FIELD

The present application generally relates to authentication. In particular, but not exclusively, the application relates to authentication using a physical unclonable function. In particular, but not exclusively, the application relates to a photoacoustic physical unclonable function.

BACKGROUND

There is an ever increasing need to be able to authenticate items, for example electronic devices, official documents, credit cards, mobile communication devices etc. The need for authentication may rise from different interests, such as detecting forgeries and copies or control of usage of items.

There is a variety of item authentication technologies available for use depending on the item. One of these techniques is the Physical Unclonable Function (PUF) that is embodied in the physical structure of the item. If a physical stimulus is applied to the physical unclonable function it reacts in an unpredictable and repeatable way to that stimulus depending on the structure.

Previous physical unclonable functions have been often found complicated to implement or they have presented security risks, such as offering a backdoor to the device being authenticated. It is an object of the present invention to mitigate the problems of PUF-authentication.

SUMMARY

Various aspects of examples of the invention are set out in the claims.

According to a first example aspect of the invention, there is provided an apparatus, comprising:
- a first element configured to receive a first signal and convert the first signal to a second signal;
- a second element configured to relay the second signal to a third element, the third element being configured to convert the second signal to a third signal and to send the third signal; wherein
- the first element is configured to convert the first signal to the second signal in such a way that the conversion is dependent on the physio-chemical structure of at least part of the first element.

The first element may comprise a photoacoustic sensor.
The first element may comprise a photoacoustic sensor comprising at least one graphene layer.
The first element may comprise a photoacoustic sensor comprising at least one graphene layer comprising at least one graphene flake or grain.
The first element may comprise a photoacoustic sensor comprising at least one graphene layer comprising at least one graphene flake or grain and at least one further material and/or at least one hole.
The second element may comprise mechanical wave transmission lines.
The second element may comprise mechanical wave transmission lines comprising a phononic bandgap transmission line.
The third element may comprise carbon nanotube antennas.
The third element may comprise carbon nanotube antennas and an infrared reflector.
The first signal may comprise electromagnetic radiation.
The first signal may comprise infrared light.
The second signal may comprise acoustic waves.
The third signal may comprise electromagnetic radiation.
The third signal may comprise infrared light.
The apparatus may be configured to operate independently when attached to a further apparatus, product or item.

According to a second example aspect of the invention, there is provided an electronic device, comprising the apparatus of the first example aspect of the invention.

According to a third example aspect of the invention, there is provided a system, comprising
- the apparatus of the first example aspect of the invention;
- a processor;
- means for sending a first signal to the first element; and
- means for receiving the third signal from the third element; wherein
- the processor is configured to cause analyzing the third signal.

The means for sending the first signal may comprise a light emitting diode.
The light emitting diode may comprise an infrared laser diode.
The means for receiving the third signal may comprise a photodetector.

According to a fourth example aspect of the invention, there is provided a method, comprising
- receiving a first signal with a first element;
- converting the first signal to a second signal with the first element;
- relaying the second signal via a second element to a third element;
- converting the second signal to a third signal with the third element;
- and sending the third signal; wherein
- converting the first signal to the second signal is dependent on the physic-chemical structure of at least part of the first element.

The first element may comprise a photoacoustic sensor.
The first element may comprise a photoacoustic sensor comprising at least one graphene layer.
The first element may comprise a photoacoustic sensor comprising at least one graphene layer comprising at least one graphene flake or grain.
The first element may comprise a photoacoustic sensor comprising at least one graphene layer comprising at least one graphene flake or grain and at least one further material and/or at least one hole.
The second element may comprise mechanical wave transmission lines.
The second element may comprise mechanical wave transmission lines comprising a phononic bandgap transmission line.
The third element may comprise carbon nanotube antennas.
The third element may comprise carbon nanotube antennas and an infrared reflector.
The first signal may comprise electromagnetic radiation.
The first signal may comprise infrared light.
The second signal may comprise acoustic waves.
The third signal may comprise electromagnetic radiation.
The third signal may comprise infrared light.
The method may further comprise sending a first signal to a first element;
receiving the third signal sent from the third element; and
analyzing the third signal.

The first signal may be sent with a light emitting diode.

The first signal may be sent with a light emitting diode comprising an infrared laser diode.

The third signal may be received with a photodetector.

According to a fifth example aspect of the invention, there is provided a computer program, comprising code for performing a method of an example aspect of the invention, when the computer program is run on a processor.

According to a sixth example aspect of the invention, there is provided a memory medium comprising the computer program of the fifth example aspect of the invention.

Different non-binding example aspects and example embodiments of the present invention have been illustrated in the foregoing. The foregoing example embodiments are used merely to explain selected aspects or steps that may be utilized in implementations of the present invention. Some example embodiments may be presented only with reference to certain example aspects of the invention. It should be appreciated that corresponding example embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Figure 1A:
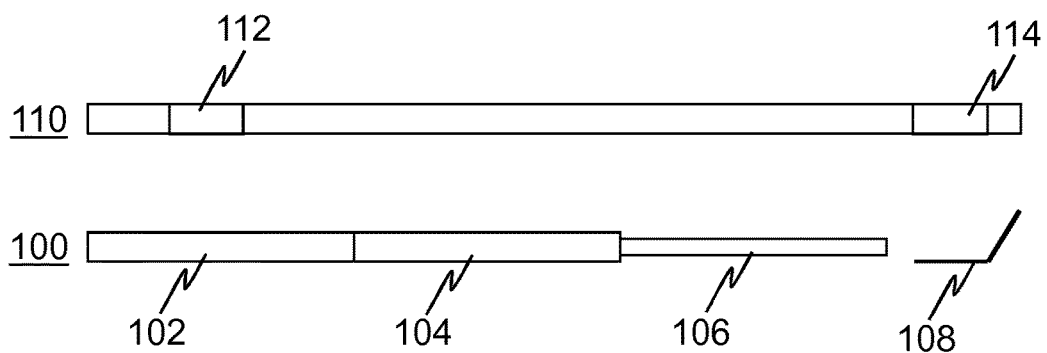
FIG. 1a shows a schematic side view of a system of an example embodiment of the invention.

FIG. 1a shows a schematic side view of the system of an example embodiment of the invention. FIG. 1a shows a Physical Unclonable Function apparatus 100. The apparatus 100 comprises a first element 102, a second element 104, and a third element 106,108. The first element, in an example embodiment, comprises a photoacoustic sensor surface, such as graphene foil, membrane or sheet comprising at least one layer of graphene. In an example embodiment the first element, i.e. the graphene sheet, is provided on a support structure. In a further example embodiment, the first element comprises a self-supporting sheet. In an example embodiment, the first element further comprises at least one graphene flake or grain, further materials and/or holes. In an example embodiment the first element comprises a graphene foil comprising a plurality of graphene layers, a plurality of graphene flakes or grain and/or defects such as introduced further materials and/or holes in order to create additional randomness into the response of the photoacoustic sensor surface. In an example embodiment, the graphene flakes or grains have a random size and/or thickness. In a further example embodiment, the edges of the first element are irregular providing additional randomness into the response. The second element 104, in an example embodiment, comprises a phononic bandgap transmission line. In an example embodiment, the second element comprises a phononic bandgap structure and a phononic steering structure for concentrating the energy to the third element. The third element 106,108, in an example embodiment, comprises at least one carbon nanotube antenna 106 and an infrared reflector. In an example embodiment, the third element 106,108 comprises metallic multi-wall nanotubes.

Figure 1B:
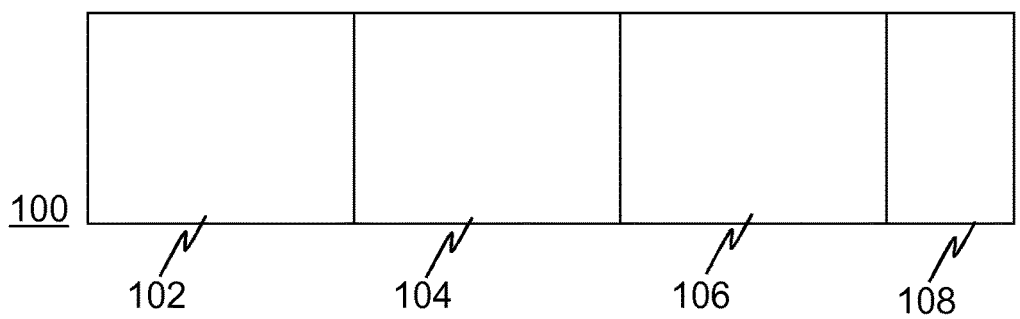
FIG. 1b shows a schematic top view of an apparatus of an example embodiment of the invention.

In an example embodiment the first element 102, i.e. the graphene foil photoacoustic sensor is configured to function as an excitation device and is configured to receive a first signal and convert it to a second signal. The second element 104 is configured to relay the second signal from the first element 102 to the third element 106,108 and the third element is configured to convert the second signal to a third signal and to send the third signal. The operation of the apparatus 100 is described in more detail hereinafter. FIG. 1b shows a top view of the apparatus 100 with the elements described hereinbefore.

The system of an example embodiment of FIG. 1a further comprises an apparatus, or a reader device, 110. The reader device comprises means 112 for sending the first signal to the first element 102 and means for receiving the third signal from the third element 106,108. In an example embodiment the means 112 comprise an infrared laser diode and the means 114 comprise a photodetector. The apparatus 110 further comprises, in an example embodiment, a processor (not shown) configured to cause analyzing of the third signal. Furthermore, a skilled person appreciates that in addition to the elements shown, the apparatus 110 may comprise other elements, such as memory, microphones, displays, as well as additional circuitry such as further input/output (I/O) circuitries, memory chips, application-specific integrated circuits (ASIC), processing circuitry for specific purposes such as source coding/decoding circuitry, channel coding/decoding circuitry, or ciphering/deciphering circuitry. Additionally, the apparatus 110 may comprise a housing and a disposable or rechargeable battery (not shown) for powering the apparatus if external power supply is not available.

Any memory referred to hereinbefore or hereinafter may comprise non-transitory non-volatile and a non-volatile memory, such as a read-only memory (ROM), a programmable read-only memory (PROM), erasable programmable read-only memory (EPROM), a random-access memory (RAM), a flash memory, a data disk, an optical storage, a magnetic storage, or a smart card. In some example embodiments, only volatile or non-volatile memory is present in the apparatus 110. Moreover, in some example embodiments, the apparatus comprises a plurality of memories. In some example embodiments, various elements are integrated. For instance, the memory can be constructed as a part of the apparatus or inserted into a slot or a port. Further still, the memory may serve the sole purpose of storing data, or it may be constructed as a part of an apparatus serving other purposes, such as processing data. Similar options are thinkable also for various other elements.

The apparatus 100, in an example embodiment, is constructed as a part of a further apparatus. In an example embodiment, the apparatus 100 is, or parts thereof are, constructed concurrently with a further apparatus, such as an electronic device. In a further example embodiment, the apparatus 100 is manufactured separately and thereinafter attached to a further apparatus, product or item, such as an electronic device or an official document. In an example embodiment, the apparatus 100, while being attached to a further apparatus, is not connected to the systems of the further apparatus, i.e. the apparatus is configured to operate independently when attached to a further apparatus, product or item in order to avoid any security risk of for example providing a backdoor access to the further apparatus.

Figure 2A:
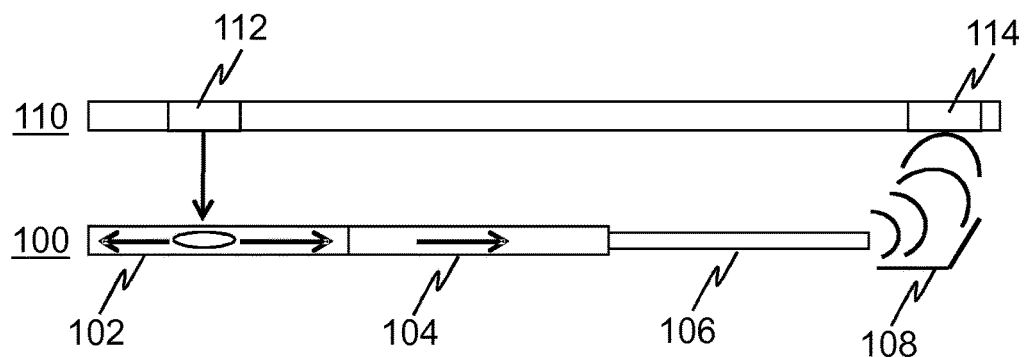
FIG. 2a shows a schematic side view of the principle of operation of a system of an example embodiment of the invention.
Figure 2B:
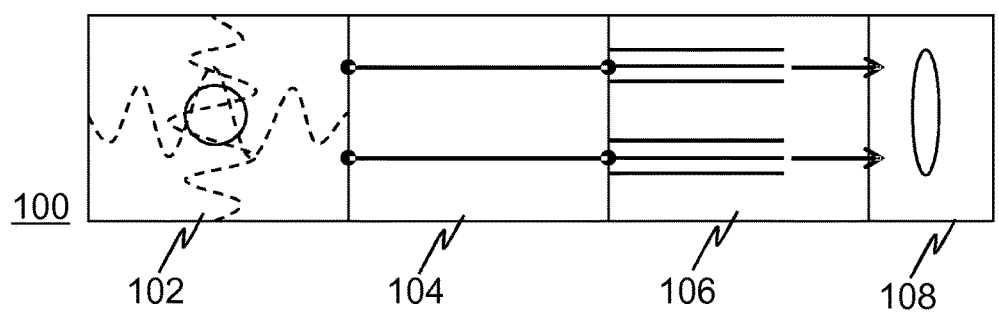
FIG. 2b shows a schematic top view of the principle of operation of an apparatus of an example embodiment of the invention.

FIGS. 2a and 2b show a schematic side and top view of the principle of operation of a system of an example embodiment of the invention. The apparatus 110 comprises means 112 for sending a first signal to the first element 102. In an example embodiment the first signal comprises electromagnetic radiation, such as infrared light. In an example embodiment, the first signal comprises an infrared laser pulse or a continuous infrared laser wave. The first signal from the apparatus 110, i.e. from the reader device, functions as a challenge to the physical unclonable function apparatus 100.

The first element 102 is configured to receive the first signal from the means 112 and to convert it to a second signal. In an example embodiment the infrared laser signal results in an ultra-high frequency, e.g. terahertz range, acoustic wave oscillating in the first element 102, i.e. in the graphene foil. The conversion of the first signal, the infrared laser signal, into the second signal, the acoustic wave, is dependent on the inherent characteristics of the first element, i.e. on the physic-chemical structure of the first element. The second element 104, the phononic bandgap transmission line, is configured to relay the second signal, the acoustic wave signal, to the third element 106, i.e. to the at least one carbon nanotube antenna. The third element 106,108 is configured to convert the second signal into a third signal, i.e. to convert the acoustic wave into infrared radiation in an example embodiment. The third element is further configured to send the third signal and further comprises in an example embodiment e.g. an infrared reflector 108.

The means 114 of the apparatus 110 is configured for receiving the third signal, i.e. the response of the physical unclonable function apparatus 100 to the first signal. The processor (not shown) of the apparatus 110 is configured to cause analyzing the third signal in order to authenticate the physical unclonable function apparatus 100. The processor is, in an example embodiment, configured to cause receiving, amplifying and digitizing the third signal and comparing to a reference signal of the physical unclonable function apparatus 100, wherein the reference signal is measured during the manufacturing of the device. In an example embodiment, the reference signal, i.e. the expected response of the apparatus 100, is retrieved from a database, for example a database containing the expected responses of items such a as passports. In an example embodiment, the identity of the apparatus, product or item to which the apparatus 100 is attached is first read electronically using for example RFID, barcode, QR-code or NFC and based on this first identification the expected response is retrieved for example from a database.

Figure 3:
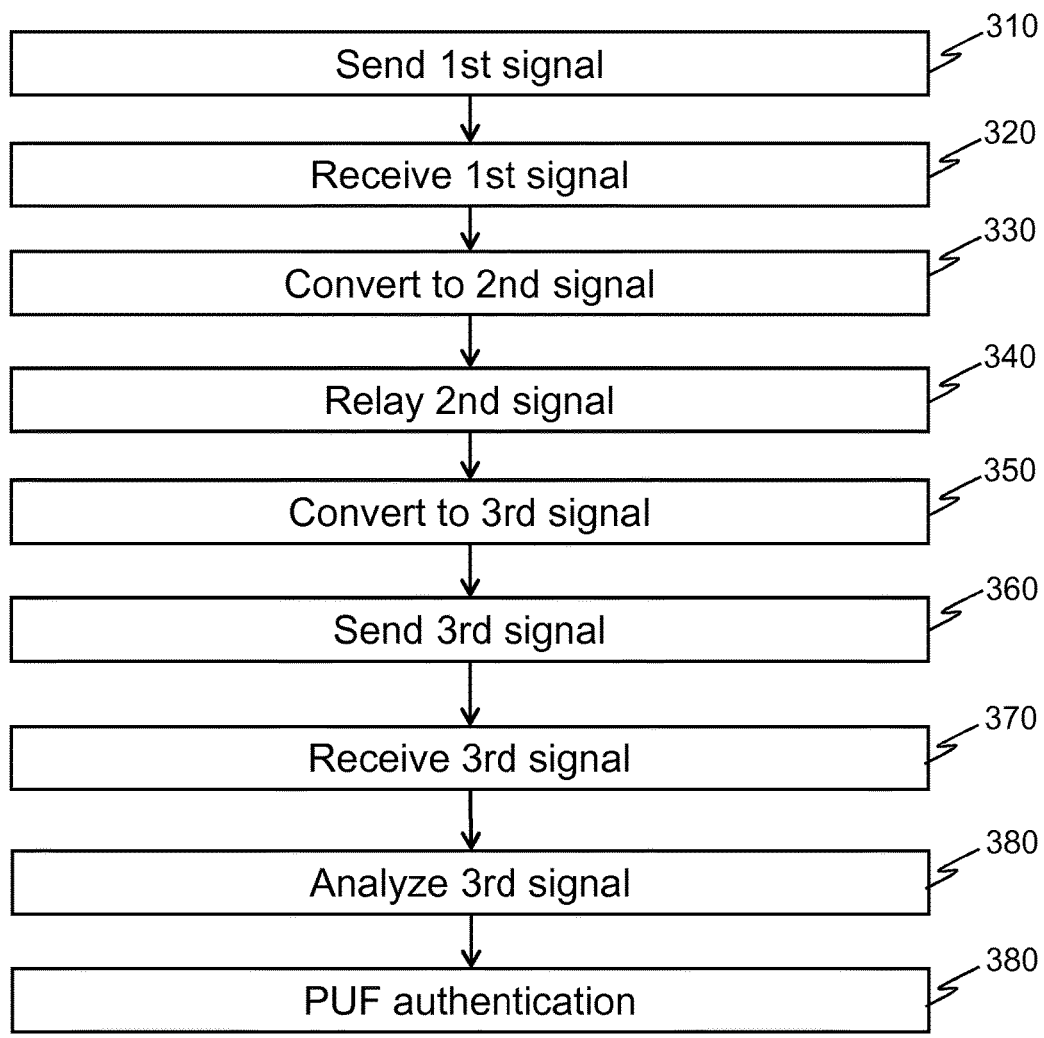
FIG. 3 shows a flow chart of a method of an example embodiment of the invention.

FIG. 3 illustrates a flow chart of an example embodiment of a method according to an example embodiment. In an example embodiment, some of the steps, i.e. the steps carried out by the apparatus 110, described are in caused to be carried out by a processor or processors of the apparatus 110, i.e. the processor is configured to cause carrying out the steps described. The steps described that are carried out in the physical unclonable function apparatus 100, do not need to be caused to be carried out by a processor, but are carried out in response to the challenge being sent to the apparatus 100.

At step 310 the apparatus 110, the reader device, sends a first signal, the challenge, to the first element 102, i.e. the graphene photoacoustic sensor, of the apparatus 100. The first element 102 receives the first signal at step 320 and converts at 330 the first signal, the infrared laser pulse or wave, into a second signal, an acoustic wave, depending on the inherent physio-chemical structure of the first element 102. At 340 the second signal is relayed by the second element 104, the phononic bandgap transmission line to the third element 106,108. The third element 106, the carbon nanotube antennas, convert the second signal into a third signal 350, i.e. convert the photoacoustic wave into infrared radiation. The third signal is sent from the third element with the help of e.g. an infrared reflector 108 comprised therein at 360.

The apparatus 110, reader device, receives the third signal at 370 and analyzes the signal at 380, i.e. compares the third signal, the response of the physical unclonable function to the challenge, with a response measured at manufacturing the physical unclonable function. At step 380 the physical unclonable function is authenticated, if the response corresponds to the one previously measured.

Without in any way limiting the scope, interpretation, or application of the claims appearing below, a technical effect of one or more of the example embodiments disclosed herein is to enable a cost effective physical unclonable function. Another technical effect of one or more of the example embodiments disclosed herein is to enable a secure authentication without risk of backgate access. Another technical effect of one or more of the example embodiments disclosed herein is to provide a way for physical unclonable function authentication using standard components and parts.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while example embodiments of the invention have been described hereinbefore, these descriptions should not be viewed in a limiting sense. Rather, there are several variations and modifications which may be made without departing from the scope of the present invention as defined in the appended claims.

The invention claimed is:
1. An apparatus comprising:
a first element, a second element, and a third element joined to one another in a series, wherein the first element is configured to receive, from an external apparatus, a first signal and to convert the first signal to a second signal, wherein the first element comprises a photoacoustic sensor, the first signal being one of an electromagnetic radiation, and the second signal being an acoustic signal;
wherein the second element is configured to relay the second signal to a third element, and the second element is a mechanical wave transmission element;
wherein the third element is configured to convert the second signal to a third signal and to send the third signal to the external apparatus, wherein the third element is at least one nanotube antenna, and the third signal is one of an electromagnetic radiation; and
wherein the first element is configured to convert the first signal to the second signal in such a way that the conversion is dependent on the physio-chemical structure of at least part of the first element, wherein the apparatus is a Physical Unclonable Function (PUF) apparatus responding to the first signal in an unpredictable and repeatable way depending on inherent characteristics of the first element, and wherein the apparatus is authenticated by the external apparatus based on the third signal.

2. The apparatus of claim 1, wherein the photoacoustic sensor comprises at least one graphene layer.

3. The apparatus of claim 1, wherein the photoacoustic sensor comprises at least one graphene layer comprising at least one graphene flake or grain.

4. The apparatus of claim 1, wherein the photoacoustic sensor comprises at least one graphene layer comprising at least one graphene flake or grain and at least one further material and/or at least one hole.

5. The apparatus of claim 1, wherein the second element comprises mechanical wave transmission lines.

6. The apparatus of claim 1, wherein the second element comprises mechanical wave transmission lines comprising a phononic bandgap transmission line.

7. The apparatus of claim 1, wherein the third element comprises carbon nanotube antennas.

8. The apparatus of claim 1, wherein the third element comprises carbon nanotube antennas and an infrared reflector.

9. The apparatus of claim 1, wherein the first signal comprises infrared light.

10. The apparatus of claim 1, wherein the third signal comprises infrared light.

11. The apparatus of claim 1 configured to operate independently when attached to a further apparatus, product or item.

12. A method comprising:
receiving, from an external apparatus, a first signal with a first element, wherein the first signal is one of an electromagnetic radiation, and the first element comprises a photoacoustic sensor;

converting the first signal to a second signal with the first element, wherein the second signal is an acoustic signal;

relaying the second signal via a second element to a third element, wherein the second element is a mechanical wave transmission element, and the third element is at least one nanotube antenna;

converting the second signal to a third signal with the third element, wherein the third signal is one of an electromagnetic radiation; and sending the third signal to the external apparatus;

wherein converting the first signal to the second signal is dependent on the physic-chemical structure of at least part of the first element, and wherein the method is performed by a Physical Unclonable Function (PUF) apparatus responding to the first signal in an unpredictable and repeatable way depending on inherent characteristics of the first element, and wherein the apparatus is authenticated by the external apparatus based on the third signal.

13. The method of claim 12, wherein the photoacoustic sensor comprises at least one graphene layer.

14. The method of claim 12, wherein the photoacoustic sensor comprises at least one graphene layer comprising at least one graphene flake or grain.

15. The method of claim 12, wherein the photoacoustic sensor comprises at least one graphene layer comprising at least one graphene flake or grain and at least one further material and/or at least one hole.

* * * * *